United States Patent
Fremy et al.

(10) Patent No.: US 10,550,077 B2
(45) Date of Patent: *Feb. 4, 2020

(54) METHOD FOR PREPARING DIMETHYL DISULPHIDE

(71) Applicant: Arkema France, Colombes (FR)

(72) Inventors: Georges Fremy, Sauveterre-de-Bearn (FR); Patrice Barre, Lons (FR); Jean-Michel Raymond, Cauneille (FR)

(73) Assignee: Arkema France, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/323,564

(22) PCT Filed: Jun. 29, 2015

(86) PCT No.: PCT/FR2015/051761
§ 371 (c)(1),
(2) Date: Jan. 3, 2017

(87) PCT Pub. No.: WO2016/001554
PCT Pub. Date: Jan. 7, 2016

(65) Prior Publication Data
US 2017/0144966 A1    May 25, 2017

(30) Foreign Application Priority Data

Jul. 4, 2014  (FR) ..................... 14 56440

(51) Int. Cl.
*C07C 319/24* (2006.01)
*C07C 319/06* (2006.01)
*C01B 32/75* (2017.01)
*C07C 319/02* (2006.01)

(52) U.S. Cl.
CPC ............ *C07C 319/24* (2013.01); *C01B 32/75* (2017.08); *C07C 319/02* (2013.01); *C07C 319/06* (2013.01)

(58) Field of Classification Search
CPC .......................... C07C 319/24; C07C 319/06
See application file for complete search history.

(56) References Cited

U.S. PATENT DOCUMENTS

| | | | | |
|---|---|---|---|---|
| 2,668,752 | A | * | 2/1954 | Folkins .................. C01B 32/70 423/443 |
| 2,788,262 | A | * | 4/1957 | Adcock .................. C01B 32/70 423/443 |
| 3,337,638 | A | | 8/1967 | Gourdon |
| 3,755,461 | A | | 8/1973 | Kvasnikoff et al. |
| 3,880,933 | A | | 4/1975 | Hubicek |
| 4,481,181 | A | * | 11/1984 | Norman .................. C01B 3/02 423/571 |
| 4,822,938 | A | | 4/1989 | Audeh |
| 5,068,445 | A | | 11/1991 | Arretz |
| 5,312,993 | A | | 5/1994 | Arretz |
| 6,743,951 | B2 | | 6/2004 | Fremy |
| 7,687,667 | B2 | | 3/2010 | Brand et al. |
| 8,008,530 | B2 | | 8/2011 | Redfingshofer et al. |
| 8,426,648 | B2 | | 4/2013 | Barre et al. |
| 8,609,576 | B2 | | 12/2013 | Redlingshofer et al. |
| 2005/0191237 | A1 | * | 9/2005 | Selinger ................... C01B 3/04 423/658.2 |
| 2007/0213564 | A1 | | 9/2007 | Yang et al. |
| 2008/0293974 | A1 | | 11/2008 | Barth et al. |
| 2010/0094059 | A1 | | 4/2010 | Yang et al. |
| 2010/0286448 | A1 | | 11/2010 | Yang et al. |
| 2011/0015443 | A1 | * | 1/2011 | Barth .................... C01B 17/161 568/71 |

FOREIGN PATENT DOCUMENTS

| | | |
|---|---|---|
| EP | 0337837 A1 | 10/1989 |
| EP | 0446109 A1 | 9/1991 |
| EP | 0976726 A1 | 2/2000 |
| GB | 1126465 A | 9/1968 |
| WO | 0196290 A1 | 12/2001 |
| WO | 2004022482 A1 | 3/2004 |

(Continued)

OTHER PUBLICATIONS

Copending U.S. Appl. No. 15/323,564, filed Dec. 27, 2016 (Year: 2016).*
Hu et al. ("Synthesis of Dimethyl Disulfide", Chemical Engineer, vol. 95, Issue 2, 2003, pp. 52-53, English translated pp. 1-10).*
International Search Report and Written Opinion for International Application No. PCT/FR2015/051761, dated Oct. 14, 2015, 10 Pages.
International Search Report and Written Opinion for International Application No. PCT/FR2015/051759, dated Oct. 10, 2015—9 Pages.
Non Final Office Action for U.S. Appl. No. 15/322,387, dated Oct. 5, 2017, 13 pages.

(Continued)

*Primary Examiner* — Rosalynd A Keys
(74) *Attorney, Agent, or Firm* — RatnerPrestia

(57) ABSTRACT

The present invention relates to a method for preparing dimethyl disulphide, in batches or continuously, preferably continuously, said method including at least the following steps: a) reacting at least one hydrocarbon feedstock in the presence of hydrogen sulphide ($H_2S$) and optionally sulphur (S) such as to form carbon disulphide ($CS_2$) and hydrogen ($H_2$); b) reacting said carbon disulphide ($CS_2$) by hydrogenation in the presence of said hydrogen ($H_2$) obtained in step a), such as to form methyl mercaptan ($CH_3SH$), hydrogen sulphide ($H_2S$) and optionally hydrogen ($H_2$); c) optionally, but preferably, recirculating said hydrogen sulphide ($H_2S$) formed in step b) to step a); d) reacting the methyl mercaptan formed in step b) with sulphur such as to form dimethyl disulphide and hydrogen sulphide; e) optionally recirculating the hydrogen sulphide formed during step d) to step a); and f) recovering the dimethyl disulphide.

20 Claims, No Drawings

(56) References Cited

FOREIGN PATENT DOCUMENTS

| WO | 2004043883 A2 | 5/2004 |
| WO | 2004096760 A1 | 11/2004 |
| WO | 2006015668 A1 | 2/2006 |
| WO | 2007028708 A1 | 3/2007 |
| WO | 2008118925 A2 | 10/2008 |
| WO | 2010046607 A1 | 4/2010 |
| WO | 2010102653 A1 | 9/2010 |
| WO | 2013029690 | 3/2013 |
| WO | 2013092129 A1 | 6/2013 |

OTHER PUBLICATIONS

Final Office Action dated Apr. 13, 2018 in U.S. Appl. No. 15/322,387, filed Dec. 27, 2016.
Non Final Office Action for U.S. Appl. No. 15/322,387, dated Oct. 5, 2018, 19 pages.
Chinese Office Action in Application No. 2015-80036343 and International Search Report issued May 28, 2018.
Hu Yongling et al., "Synthesis of Dimethyl Disulfide", Chemical Engineer 2:52-53 (2003).
Final Office Action for U.S. Appl. No. 15/322,387, dated Jun. 14, 2019, 16 pages.
Hosseini et al., "Carbon Disulfide Production via Hydrogen Sulfide Methane Reformation", International Journal of Chemical and Molecular Engineering, 2010, vol. 4, No. 2, pp. 198-201.

* cited by examiner

METHOD FOR PREPARING DIMETHYL DISULPHIDE

CROSS-REFERENCE TO RELATED APPLICATIONS

This is the national phase of International Application No. PCT/FR2015/051761, filed 29 Jun. 2015, which claims priority to French Application No. 1456440, filed 4 Jul. 2014. The disclosure of each of these applications is incorporated herein by reference in its entirety for all purposes.

FIELD OF THE INVENTION

The present invention relates to a process for preparing dimethyl disulphide (the acronym for which, used hereinafter, is DMDS) from a hydrocarbon charge, hydrogen sulphide and sulphur.

BACKGROUND OF THE RELATED ART

Disulphides, and especially dimethyl disulphide, are of great industrial interest and are nowadays very widely used in industry, for example and non-limitatively as an additive for sulphurizing catalysts, especially for hydrotreating petroleum fractions, or else as a soil fumigation agent in agriculture.

DMDS is nowadays commonly produced industrially on the tonne scale by reaction of sulphur with methyl mercaptan, as described for example in documents EP337837 and EP446109.

Methyl mercaptan may itself be produced from methanol ($CH_3OH$) and hydrogen sulphide ($H_2S$) in accordance with the following reaction (1):

$$CH_3OH + H_2S \rightarrow CH_3SH + H_2O \quad (1)$$

This synthesis pathway, however, has a number of drawbacks, including that of using methanol, which necessitates a supplementary step, since methanol is prepared from hydrocarbon charges, and the drawback of leading to secondary products, typified especially by dimethyl ether ($CH_3OCH_3$), dimethyl sulphide ($CH_3SCH_3$), and cracking products (such as, for example, carbon monoxide and carbon dioxide), and water, to state only some of the drawbacks. Moreover, the presence of secondary products of these kinds results in a large number of purification steps for the methyl mercaptan, to the detriment of high productivity and high selectivity and therefore of an optimum yield.

This synthesis pathway, and also some improvements thereto, are described for example in documents WO2004/096760, WO2006/015668, WO2007/028708, WO2008/118925 and WO2013/092129.

Other synthesis processes do away with the need to use methanol, and include the preparation of methyl mercaptan from carbon monoxide (CO) in accordance with the following reaction (2):

$$CO + 2H_2 + H_2S \rightarrow CH_3SH + H_2O \quad (2)$$

However, the use of carbon monoxide (CO) is not free of drawbacks, since CO originates essentially from synthesis gas, which is a $CO/H_2$ mixture, and which consequently necessitates:

a supplementary step of steam reforming of a hydrocarbon source for the purpose of obtaining a synthesis gas,
the availability of a synthesis gas having appropriate proportions of carbon monoxide (CO) and hydrogen ($H_2$), without any need for adjustment to the $CO/H_2$ ratio by means of the water-gas shift reaction, defined as follows in reaction (A):

$$CO + H_2O \rightarrow CO_2 + H_2 \quad (A)$$

Moreover, the processes in accordance with reaction (2) above have the drawback of giving rise to secondary products, such as carbon dioxide ($CO_2$), methane ($CH_4$), dimethyl sulphide ($CH_3SCH_3$) and water ($H_2O$). These processes are described for example in documents US2007213564, US2008293974, US2010094059, and US2010286448.

Yet other processes are described in the literature, and combine different reactions, such as:

formation of $CS_2$ and $H_2S$ from methane and sulphur, in accordance with reaction (3):

$$CH_4 + 4S \rightarrow CS_2 + 2H_2S \quad (3)$$

hydrogenation of $CS_2$, using the hydrogen formed above, in accordance with reaction (4):

$$CS_2 + 3H_2 \rightarrow CH_3SH + H_2S \quad (4)$$

These processes evidently combine the drawbacks described for reactions (1) and (2) with the additional difficulty of necessitating a supplementary source of hydrogen in order to perform reaction (4).

Yet another method is disclosed in document WO2010/046607 and involves the hydrogenation of sulphur compounds which carry C=S unsaturation, and more particularly the hydrogenation of carbon disulphide ($CS_2$), to methyl mercaptan ($CH_3SH$) in accordance with reaction (4) above.

However, the process performed in this document employs carbon disulphide ($CS_2$), which is a dangerous, toxic product which can be used industrially with the installation of severe safety means; all enterprises and factories do not wish to or are unable to develop a plant meeting the safety standards required for the holding of carbon disulphide.

International patent application WO2001/96290 proposes a process for synthesis of methyl mercaptan directly from methane ($CH_4$) and $H_2S$ with co-production of hydrogen. This direct reaction between methane and $H_2S$ is accomplished by means of a pulsed plasma with corona discharge. This patent application does not describe any example of synthesis, and it does not appear possible to envisage the industrial-scale implementation of this process for synthesizing methyl mercaptan. Moreover, this process requires the synthesis of $H_2S$ if the latter is unavailable.

Today, therefore, there is a need for a process for synthesis of DMDS by reaction of sulphur with methyl mercaptan that does not exhibit the drawbacks encountered in the known processes, thus being more environmentally friendly and less eco-toxic, but also safer, while preserving the high yields and selectivities, or even with yields and selectivities which are improved relative to those of the known processes, while being a process which is operated as economically as possible.

SUMMARY OF THE INVENTION

It has now been found that it is possible to remove the aforementioned drawbacks, entirely or at least partly, by virtue of the process for preparing dimethyl disulphide (DMDS) in accordance with the present invention, which is detailed in the description hereinafter. The process of the present invention makes it possible more particularly to resolve a large number of the drawbacks in the processes based on reactions (1) and (2) as described above.

Accordingly, in a first aspect, the present invention provides a process for preparing dimethyl disulphide, batchwise or continuously, preferably continuously, said process comprising at least the following steps:

a) reaction of at least one hydrocarbon charge in the presence of hydrogen sulphide ($H_2S$) and optionally of sulphur (S) to form carbon disulphide ($CS_2$) and hydrogen ($H_2$),
b) hydrogenation reaction of said carbon disulphide ($CS_2$) in the presence of said hydrogen ($H_2$), both obtained in step a), to form methyl mercaptan ($CH_3SH$), hydrogen sulphide ($H_2S$) and optionally hydrogen ($H_2$),
c) optionally, but preferably, recycling said hydrogen sulphide ($H_2S$) formed in step b) to step a),
d) reaction of the methyl mercaptan formed in step b) with sulphur to form dimethyl disulphide and hydrogen sulphide,
e) optionally recycling into step a) of the hydrogen sulphide formed in step d), and
f) recovery of the dimethyl disulphide.

This process has the very great advantage of consuming the hydrogen sulphide ($H_2S$) which is produced during the reaction, and in some cases even doing so stoichiometrically as indicated later on below, hence meaning that all the hydrogen sulphide consumed in the process of the invention is produced by said process.

Therefore, the process of the invention avoids any addition, and even in some cases any removal, of hydrogen sulphide ($H_2S$) in excess, or else avoids the additional synthesis of hydrogen sulphide ($H_2S$), as is sometimes required with the known processes of the prior art.

Moreover, the process of the present invention is a process which is simple to perform, is of low eco-toxicity and is economical. The process of the invention also makes it possible to obtain a high yield and a high selectivity in terms of DMDS. In the present description, unless otherwise stated, the percentages referred to are percentages by weight.

DETAILED DESCRIPTION OF CERTAIN EMBODIMENTS OF THE INVENTION

The process according to the invention is a process of three consecutive reaction steps (steps a), b) and d) above), without any need for the intermediates obtained in each step to be purified. Schematically, the first step of the process (step a) is a reaction, carried out preferably at high temperature, between a hydrocarbon charge (illustrated here: methane) and hydrogen sulphide ($H_2S$) in accordance with reaction (5):

$$CH_4 + 2H_2S \rightarrow CS_2 + 4H_2 \quad (5)$$

In the second step (step b)), the carbon disulphide formed in step a) is subjected to catalytic hydrogenation with the hydrogen likewise formed in step a), in accordance with reaction (6):

$$CS_2 + 4H_2 \rightarrow CH_3SH + H_2S + H_2 \quad (6)$$

This succession of two reaction steps is notable in that the number of mols of methyl mercaptan formed is identical to the number of mols of methane consumed, and that step a) (reaction 5) requires twice as many mols of hydrogen sulphide as formed in step b) (reaction 6).

In one especially advantageous embodiment of the present invention, the hydrogen sulphide formed in step b) is recycled into step a) according to step c). In this embodiment, it is seen that all of the hydrogen sulphide formed may therefore be re-used in step a), avoiding the storage of said hydrogen sulphide formed.

In another embodiment, the sulphurized hydrogen (or hydrogen sulphide) formed at the end of step b) may not be recycled into step a), and may be recovered for subsequent use—for example, may be passed into the step e) of recycling of the hydrogen sulphide formed after the reaction of the sulphur with methyl mercaptan.

As indicated above, the amount of hydrogen sulphide produced in step b) (reaction (6) above) is not sufficient in molar amount for the implementation of reaction (5) in step a), and a further amount of hydrogen sulphide must be supplied in order for step a) to be conducted. This further amount may originate, for example, from the hydrogen sulphide which is formed after the reaction of the sulphur with methyl mercaptan and which may be recycled according to step e).

As a variant, consideration may also be given to synthesizing the missing amount of hydrogen sulphide, especially from the hydrogen formed in step b) reacted with sulphur according to the process described for example in document WO2004/022482, in accordance with the following reaction (B):

$$S + H_2 \rightarrow H_2S \quad (B)$$

The methyl mercaptan is formed in step b) and, after optional recycling of the hydrogen sulphide ($H_2S$) in step c), is subsequently reacted with sulphur by the conventional methods known to the skilled person, for example as described in EP0976726, in accordance with the following reaction scheme (8):

$$2CH_3SH + S \rightarrow CH_3SSCH_3 + H_2S \quad (8)$$

The reaction of methyl mercaptan with sulphur to form dimethyl disulphide is definitely of interest, not least from the economic standpoint, owing to the simultaneous formation of hydrogen sulphide, which may certainly and advantageously be recycled into step a) of the process of the invention for synthesis of methyl mercaptan.

According to a variant of the process of the invention, the sulphur may be introduced in the first step (step a)). The balanced reaction may then be written in accordance with scheme (9) below:

$$CH_4 + S + H_2S \rightarrow CS_2 + 3H_2 \quad (9)$$

and step b) of the process may then be illustrated by the reaction scheme (4):

$$CS_2 + 3H_2 \rightarrow CH_3SH + H_2S \quad (4)$$

In this case, the entirety of the hydrogen sulphide produced in step b) in accordance with the reaction of scheme (4) may advantageously be recycled entirely (stoichiometry respected) in step a) (in scheme (9)), this avoiding the supplementary synthesis of hydrogen sulphide with supplementary equipment.

Accordingly, and depending on whether step a) does not comprise the addition of sulphur or does comprise the addition of sulphur, and with consideration of the overall mass balance, the process according to the invention has the very great advantage of producing one mole of methyl mercaptan per mole of methane consumed. The embodiments of the present invention may be schematized as is illustrated respectively by reaction schemes (α) and (β) below:

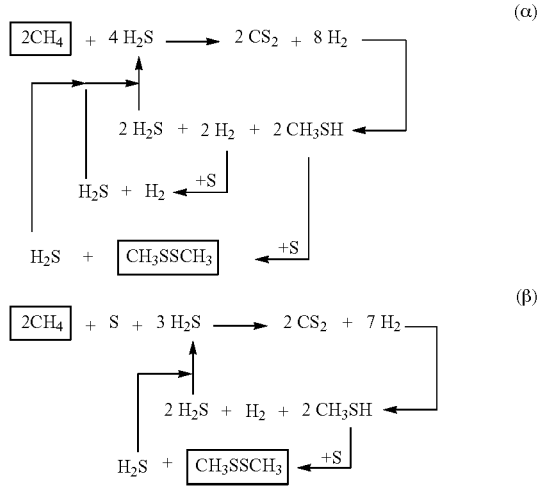

with the proviso that in these schemes, the recycling of the hydrogen sulphide is optional, and that the synthesis of hydrogen sulphide from hydrogen and sulphur is also optional.

All of the above reactions involve methane ($CH_4$) as initial hydrocarbon charge, but the process of the invention may be carried out in a similar manner from any type of hydrocarbon charge. For a hydrocarbon charge of type $C_aH_{2b}$, the general equation corresponding to the reaction of the first step (step a)) then becomes:

$$C_aH_{2b} + 2aH_2S \rightarrow aCS_2 + (2a+b)H_2$$

where $\underline{a}$ is an integer preferably between 1 and 30, end points included, more preferably between 1 and 20, end points included, more preferably between 1 and 10, end points included, and $\underline{b}$ represents an integer between $\underline{a}/2$ and $2(\underline{a}+1)$, end points included, with the restriction that when $\underline{a}$ represents 1, then $\underline{b}$ represents 2.

Accordingly, and as an illustrative example, when the hydrocarbon charge is propane ($C_3H_8$, $\underline{a}=3$ and $\underline{b}=4$), for example, the potential products obtained would be 3 $CS_2$ and $10H_2$.

Accordingly, the hydrocarbon charge reacted with hydrogen sulphide ($H_2S$) in step a) may be any type of charge known to the skilled person, and is generally a hydrocarbon charge in gaseous, liquid or solid form, preferably in gaseous or liquid form, more preferably in gaseous form, and comprises at least one hydrocarbon having a hydrocarbon chain in saturated or unsaturated linear, branched or cyclic form.

More preferably, the hydrocarbon filler comprises at least one alkane, preferably at least methane ($CH_4$), ethane, propane or butane, and very preferably methane. With further advantage the hydrocarbon charge is pure, meaning that it contains a single compound, for example an alkane, and preferably methane ($CH_4$), ethane, propane or butane, and very preferably methane.

The above-defined hydrocarbon charge may come from numerous sources, all of which are known to the skilled person, whether natural, artificial or synthetic, for example from natural sources, but also by direct synthesis, by metathesis, etc. Examples of sources of hydrocarbon charge which can be used in the process of the present invention include, illustratively and not limitatively, biomass, petroleum, charcoal, coal, bituminous shales, bituminous sands, and others.

According to one especially preferred aspect, the hydrocarbon charge employed in step a) is selected from natural gas, shale gas and shale oil. The sources of hydrocarbon charges are preferably selected from natural gas, shale gas and biogas.

Other examples of sources of hydrocarbon charges which may advantageously be used in the context of the present invention include naphthas, crude petroleum distillation products, petroleum fractions, preferably demetallized, deoxygenated and/or denitrogenated, decomposition products, and more particularly products of the natural or industrial methanization of biomass.

Nevertheless, in the context of the present invention, preference is given to using methane as initial hydrocarbon charge, primarily for economic reasons, particularly with the recent developments in the exploitation of shale gas.

The methane used as initial hydrocarbon charge may be employed with one or more other gases, different from the hydrocarbon charges as described above, although for obvious reasons of subsequent purification, and ease of implementation of the process (risk of accumulation with any recycling operations), preference will be given to using only mixtures of hydrocarbon charges or pure methane.

Where pure methane is used, but also when the initial hydrocarbon charge is other than methane alone, there are no real constraints in terms of the molar $H_2S/CH_4$ ratio, or $H_2S$/hydrocarbon charge ratio, that can be used in step a), since the excess of $H_2S$ is advantageously recycled at the end of step b). If a hydrogen sulphide is used in a substoichiometric amount, the effect will be seen in the conversion of the methane, or of the hydrocarbon charge, respectively, and of the production of hydrogen.

It is also possible to consider not using $H_2S$ in the first step, and generating the required $H_2S$ in situ by reacting the hydrocarbon charge with sulphur according to reaction (3) defined above. The molar $H_2S$/hydrocarbon charge ratio may therefore be 0 (if sulphur is present) and may be up to about 100, the molar ratio preferably being between 0.5 and 10 and more preferably between 1 and 3, these ranges of values being understood with end points included. These values are particularly suitable when the initial hydrocarbon charge is methane or comprises methane.

The hydrocarbon charge and the hydrogen sulphide are advantageously provided continuously or discontinuously in the reactor or reactors in which the process/the invention is implemented, depending more particularly on whether the process is implemented continuously or batchwise. The hydrocarbon charge and the hydrogen sulphide are advantageously in liquid or solid or gaseous form, preferably in gaseous form.

According to one embodiment, step a) is implemented in the absence of sulphur, corresponding to the process of the invention in accordance with scheme (a). According to another embodiment, step a) is implemented in the presence of sulphur, this corresponding to the process of the invention in accordance with scheme (13). In this embodiment, the sulphur is in liquid, solid or gaseous form, preferably in liquid or gaseous form.

The process according to the present invention, moreover, offers the great advantage of generating an excess of hydrogen, irrespective of the embodiment, (α) or (β), it being possible for this hydrogen to be separated from the reaction mixture and exploited. A particularly advantageous form of exploitation for the hydrogen formed is its combustion with oxygen to provide the thermal energy required for the various steps in the process of the invention, particularly for the heating for the reaction of step a), which requires high temperatures for industrially acceptable performance levels.

Accordingly, and in accordance with a further aspect, the invention relates to a process for synthesizing dimethyl disulphide as defined above, in which the hydrogen co-produced is wholly or partly converted into thermal energy, for example by combustion (in oxygen or in air, for example), it being possible for this thermal energy to be used for the heating of the reaction or reactions of step a), of step b) and/or of step d), preferably of step a).

According to one embodiment, step a) is carried out in the presence of a catalyst. In this embodiment, said catalyst advantageously comprises a transition metal selected from the elements of groups 6 to 11 of the Periodic Table of the elements (groups VIB, VIIB, VIIIB), preferably from the elements of groups 6, 9 and 10, and more preferably the catalyst comprises one or more transition metals selected from platinum, rhodium, chromium and palladium. More preferably the catalyst comprises one or more transition metals selected from platinum, rhodium, chromium or palladium, and very preferably the catalyst comprises platinum.

Accordingly, the catalyst of step a) comprises a metal or metals, it being possible for these metals to be in the form of a mixture, and it being possible for said metal (or metals) to be in metallic form, but also in the form of oxide(s) or sulphide(s). When the catalyst is present in the form of a metal oxide, a sulphurizing step may advantageously be carried out according to the methods known to the skilled person.

The catalyst used in step a) is preferably a supported catalyst, the support being selected preferably from alumina, silica, zeolites, activated carbons, titanium oxide, zirconium oxides, clays, hydrotalcite, hydroxyapatite, magnesia, and others. The catalyst may be favourably used in a fixed, fluid, circulating or ebullating bed. The catalyst is preferably used in a fixed bed. According to another embodiment, step a) is carried out in the absence of catalyst.

The reaction temperature in step a) is advantageously between 500° C. and 1300° C., preferably between 700° C. and 1100° C., more preferably between 800° C. and 1000° C. For conversion reasons, for the lower limit, and for reasons of resistance of materials, for the upper limit, preference is given to a temperature range between 700° C. and 1100° C., preferably between 800° C. and 1000° C.

The reaction of step a) may be carried out alternatively at atmospheric pressure, under superatmospheric pressure, or even under subatmospheric pressure; the skilled person is aware of how to adapt the reaction pressure conditions according to the nature of the reactants employed, the reaction temperatures selected, the rates of circulation of the streams, and the intended degrees of conversion and intended yields.

Generally speaking, step a) may be carried out under a pressure of between 50 mbar and 100 bar (i.e. between $5 \times 10^3$ and $1 \times 10^7$ Pa), more preferably between atmospheric pressure and 50 bar (or $5 \times 10^6$ Pa), and advantageously between atmospheric pressure and 15 bar (or $15 \times 10^5$ Pa).

The duration of the reaction in step a) may vary within wide proportions, depending in particular on the nature and amount of each of the reactants, the nature and amount of catalyst used, and the selected temperature and pressure. Generally speaking, the reaction time in step a) may vary between several seconds to several minutes.

When sulphur is present for the implementation of the reaction in step a), the molar sulphur/$CH_4$ ratio is preferably between 0 and 4, end points excluded, or more generally the molar sulphur/hydrocarbon charge ratio is preferably between 0 and (2a+b), end points excluded, where a and b are as defined above.

A molar sulphur/$CH_4$ ratio of 4 or more, in view of reaction (3), could bring about the complete conversion of the methane to $CS_2$ and $H_2S$, this being undesirable for step b) of the process, which requires hydrogen. According to one preferred aspect of the present invention, therefore, the sulphur/$CH_4$ ratio is between 0 and 4, end points excluded, preferably between 0 and 2.5, end points excluded, and more preferably between 0 and 1.5, end points excluded.

As indicated above, the process according to the invention removes the need for a purification step between steps a) and b). The reason for this is that during the implementation of step b), the hydrogen ($H_2$) and the carbon disulphide ($CS_2$) that are obtained in step a) react together directly to form hydrogen sulphide ($H_2S$) and methyl mercaptan ($CH_3SH$), and optionally hydrogen ($H_2$). Accordingly, the respective ratios of the reactants employed in step b) are directly dependent on the ratios of the products obtained at the end of step a).

The conduct of the reaction in step b) is known to the skilled person and is described for example in international patent application WO2010/046607. This reaction is therefore known to lead to a conversion of $CS_2$ of 100% for a selectivity in terms of methyl mercaptan of 100%, if hydrogen is present at stoichiometry or in excess. The consequence is that the methyl mercaptan produced in this step b) is very easy to separate from the reaction mixture, since this mixture contains only methyl mercaptan, $H_2S$, hydrogen, if it was in excess, and optionally the hydrocarbon charge which may be in excess in step a), to have a complete conversion of the sulphur. It should be noted that the hydrocarbon charge in excess, after passing inertly into step b) and after separation of the methyl mercaptan formed, may be recycled to step a) with the $H_2S$.

According to one embodiment, step b) may be carried out in the presence of a catalyst. In one preferred embodiment, a catalyst is used for the hydrogenation of the carbon disulphide to methyl mercaptan. The catalyst which may be used may be of any type known to the skilled person as a hydrogenation catalyst. Advantageously, the catalyst used for step b) of the process according to the present invention may be selected from those described in international patent application WO2010/046607, in which said hydrogenation catalyst comprises at least one metal doped with at least one alkali metal or alkaline-earth metal hydroxide or oxide.

The metal present in the catalyst of the invention may be any metal from group 6 and/or 8 of the Periodic Table of the classification of the Elements (IUPAC), and is preferably selected from the group consisting of nickel (Ni), cobalt (Co), palladium (Pd), rhodium (Rh), platinum (Pt), molybdenum (Mo), tungsten (W), chromium (Cr), iron (Fe) and combinations of two or more of these, preferably combinations of two of these metals, and more particularly Co/Mo, Ni/Mo, Ni/W, W/Mo, with very particular preference being given to the combinations of nickel and molybdenum.

The metal or metals present in the catalyst of the invention may also be present directly in the form of metal sulphides. These metal sulphides may also be obtained from the corresponding oxides by any method known to the skilled person.

The catalyst of the invention is advantageously supported, conventionally, on any type of support generally used within this field, and for example on a support selected from alumina, silica, titanium dioxide ($TiO_2$), zeolites, carbon, zirconium, magnesia (MgO), clays, hydrotalcites and others, and also mixtures of two or more thereof.

As for the catalyst used in step a), the catalyst employed is favourably used in a fixed, fluidized, circulating or ebullating bed. The catalyst is preferably in a fixed bed.

The amount of catalyst used in step a) and the amount of catalyst used in step b) are dependent on the amount of methyl mercaptan it is desired to obtain. Accordingly, the amounts of catalyst(s) employed in steps a) and b) are adjusted with the aim of obtaining a methyl mercaptan productivity of from 0.1 kg·h$^{-1}$ to 20 kg·h$^{-1}$ per liter of catalyst. In this configuration, the process according to the present invention has proved to be of particular interest in terms of industrial and economic profitability. According to another embodiment, step b) is carried out without catalyst.

The reaction temperature in step b) is generally lower than that used in step a), and is commonly between 100° C. and 400° C. and preferably between 200° C. and 300° C., a temperature range within which the maximum selectivity in terms of methyl mercaptan is observed, for an optimum conversion.

As for step a), step b) may be carried out under any pressure, preferably of between 50 mbar and 100 bar (i.e. between $5\times10^3$ Pa and $1\times10^7$ Pa) more preferably of between atmospheric pressure and 50 bar (or $5\times10^6$ Pa) and advantageously between atmospheric pressure and 15 bar (or $15\times10^5$ Pa).

The hydrogenation time varies according to the nature and amount of each of the reactants, and the nature and amount of catalyst used. For example, the reaction varies between several seconds and several minutes.

As indicated above, step d), the step of reacting sulphur with methyl mercaptan to produce dimethyl disulphide and hydrogen sulphide, may be carried out according to any method known to the skilled person, and the hydrogen sulphide formed may be recycled to step a) or to step c). The operating conditions for the implementation of step d) are described for example in EP0976726.

Steps a), b) and d) may be implemented in any type of reactor suitable for receiving high-temperature reactions, as for example reactors made of alloy, of Hastelloy, Incoloy and other types.

According to one preferred embodiment, steps a), b) and d) are each employed in a separate reactor. According to another embodiment, steps a), b) and d) are carried out in succession in the same reactor.

As indicated above, the process according to the invention optionally, but preferably, comprises a step c) of recycling of the hydrogen sulphide formed at the end of step b), which is re-introduced into the initial charge for realization of step a). This step c) of recycling of the hydrogen sulphide formed has the advantage that in this way it is possible to avoid the ex situ synthesis of hydrogen sulphide.

Similarly, the process according to the invention optionally, but preferably, comprises a step e) of recycling of the hydrogen sulphide formed at the end of step d), which is re-introduced into the initial charge for realization of step a) and/or is re-introduced into the hydrogen sulphide recycled to step c).

Hydrogen sulphide may therefore be recycled after separation from the reaction mixture from step b) and/or from step d), according to any method known to the skilled person, and, for example, by distillation, preferably under pressure, by freezing, by membrane separation, etc.

Step f), the step of recovering dimethyl sulphide, may be carried out according to any method known per se, and, for example, by degassing of the more volatile compounds, such as hydrogen and hydrogen sulphide. Any unconverted hydrocarbon charge, and also any unconverted carbon disulphide and/or sulphur, are separated from the methyl mercaptan by distillation.

The entirety of the remaining reaction mixture from step d) (from which the DMDS has been removed) may advantageously be re-introduced recycled into step a) of the process. This embodiment has the advantage of also recycling the initial hydrocarbon charge, thereby allowing a substantial improvement in the DMDS production yield in relation to the hydrocarbon charge introduced at the start. The process is optimized in this way, since each carbon atom present in the initial hydrocarbon charge is converted into half a mol of methyl mercaptan.

Accordingly, and in accordance with one variant, the process according to the invention comprises not only the recycling of the hydrogen sulphide but also the recycling of the residual compounds, in other unreacted compounds, these being carbon disulphide, optionally hydrogen, optionally the hydrocarbon charge, optionally sulphur, and optionally impurities. Generally speaking, the recycling is carried out according to techniques which are well known to the skilled person.

It has been observed, moreover, that when coke is formed during the implementation of the process according to the invention, it reacts with the hydrogen sulphide (and optionally the sulphur present) to form hydrogen and carbon disulphide. The process according to the invention therefore has the very great advantage of being operated as a perfectly autonomous system, without harmful emission of hydrogen sulphide, and without harmful formation of coke in the reactor, in spite of the presence of hydrocarbon charge at high temperature.

The present invention therefore offers an industrial process for preparation of DMDS that is completely autonomous, has a high yield, and is more environment-friendly and more economical than the methods known in the prior art.

In one variant of the process of the invention, when the by-products are not recycled, or when only the hydrogen sulphide is recycled, it is possible to exploit said by-products—hydrogen sulphide, hydrogen and optionally carbon disulphide. One use of particular interest for the hydrogen formed during the process of the invention is its use with liquid sulphur to form hydrogen sulphide, which may therefore be used in the process of the invention, as already indicated above.

By virtue of the aforementioned advantages of the process according to the present invention, it is possible to achieve a high methyl mercaptan productivity, generally of the order of 0.1 kg to 20 kg of methyl mercaptan per hour per liter of catalyst in step b), the methyl mercaptan being subsequently converted to DMDS (step d)) after optional recycling of the hydrogen sulphide formed (step c).

According to one preferred embodiment, the hydrogen sulphide formed in step c) is recycled into step a). According to another preferred embodiment, the process according to the invention comprises a step e) in which the hydrogen sulphide in step d) is recycled into step a). According to yet another preferred embodiment, the hydrogen sulphide from step c) and the hydrogen sulphide from step e) are recycled into step a). According to yet a further preferred embodiment, the hydrogen sulphide from step e) is recycled into step c).

It has been shown accordingly that the process for synthesis of dimethyl disulphide according to the present invention offers a very great number of advantages over the known processes of the prior art, more particularly the advantage of not requiring the use of methanol, thereby resulting in lower production costs.

The present invention is now illustrated using examples below, which do not have any limitative character and which therefore cannot be understood as being able to restrict the scope of the invention as it is claimed.

EXAMPLES

For each of the examples, the reaction products and the products which have not reacted are vaporized and analysed by gas chromatography with a capillary column equipped with a detector (microGC, screen/PPU column in series with a PoraPLOT column from Agilent Technologies, µTCD detector).

In the examples below, the degrees of conversion and selectivity are determined as follows:

Degree of molar conversion of $CH_4$ (% $C_{CH4}$):

% $C_{CH4}=[(n_{0CH4}-n_{CH4\ residual})/n_{0CH4}]*100$ where $n_{0CH4}$ is the initial number of moles of $CH_4$ and $n_{CH4\ residual}$ is the number of moles of unreacted $CH_4$.

Degree of molar conversion of $CS_2$ (% $C_{CS2}$):

% $C_{CS2}=[(n_{0CS2}-n_{CS2\ residual})/n_{0CS2}]*100$ where $n_{0CS2}$ is the initial number of moles of $CS_2$ and $n_{CS2\ residual}$ is the number of moles of unreacted $CS_2$.

Molar selectivity for $CH_3SH$ (% $SCH_3SH$):

% $S_{CH3SH}=[n_{CH3SH}/(n_{0CS2}-n_{CS2\ residual})]*100$ where $n_{CH3SH}$ is the number of moles of $CH_3SH$ produced during the process according to the invention.

Molar selectivity for $CS_2$:

% $S_{CS2}[n_{CS2}/(n_{0CH4}-n_{CH4\ residual})]*100$ where $n_{CS2}$ is the number of moles of $CS_2$ produced during the process according to the invention.

Example 1

An Incoloy® 800 HT reactor containing 12 grams of catalyst containing 0.5% by weight of platinum on alumina, sold by STREM is placed in an oven. The catalyst is intercalated between two layers of carborundum.

The reactor is supplied with 20 NL·h$^{-1}$ (or 893 mmol·h$^{-1}$) of hydrogen sulphide ($H_2S$) and 10 NL·h$^{-1}$ (or 446 mmol·h$^{-1}$) of methane ($CH_4$). These two gases are preheated independently to 500° C. before entering the reactor. The reactor is brought to a temperature of 900° C. by means of the oven, and the pressure at the outlet of the reactor is regulated at 3 bar absolute. The flow rate of the exiting gases, taken under the standard conditions of temperature and pressure, in other words 0° C. and 1 atmosphere (101325 Pa), is 37.5 NL·h$^{-1}$.

Gas-chromatographic analysis of the exiting gases indicates the presence of four gases: unconverted $CH_4$ and $H_2S$, and also $CS_2$ and $H_2$, which have been produced with a molar $H_2/CS_2$ ratio of 4. Under these conditions, the molar conversion of $CH_4$ is 32%, with a selectivity for $CS_2$ of 100%.

These exiting gases, after cooling to a regulated temperature of 250° C., are introduced into a second reactor, containing 50 mL of NiMo/alumina catalyst (HR448, sold by Axens), doped with 11.6% of $K_2O$ (according to the "Cata 3" preparation described in patent application WO2010/046607). The pressure is 3 bar (0.3 MPa) absolute in the oven, at 250° C. Gas-chromatographic analysis of the exiting gases shows that the $CS_2$ has been completely converted (100%) with a selectivity of 100% for methyl mercaptan, in other words each molecule of carbon disulphide has been converted to methyl mercaptan in accordance with reaction (4). The reaction mixture also comprises hydrogen sulphide, hydrogen, and the unreacted methane. The entirety of these compounds may be recycled into step a).

Example 2

Example 1 was repeated, this time adding 5.7 g·h$^{-1}$ of sulphur (or 178 mmol·h$^{-1}$) to the 10 NL·h$^{-1}$ of methane (or 446 mmol·h$^{-1}$) and with a reduction in the 20 NL·h$^{-1}$ of $H_2S$ to 10 NL·h$^{-1}$ (446 mmol·h$^{-1}$). The sulphur is introduced in liquid form at 130° C. with the other reactants, at the top of the reactor, the internal reactor temperature being maintained at a temperature of 900° C. and the internal pressure at 3 bar (3×10$^5$ Pa) absolute. The flow rate of the exiting gases, taken under standard conditions of temperature and pressure, is 28 NL·h$^{-1}$.

Gas-chromatographic analysis of the exiting gases indicates the following molar composition: $CH_4$: 21% (or 262 mmol·h$^{-1}$), $H_2S$: 22% (or 275 mmol·h$^{-1}$), $CS_2$: 14% (or 175 mmol·h$^{-1}$) and $H_2$: 43% (or 537 mmol·h$^{-1}$).

The mass balance realized with these analyses indicates that sulphur has been converted to 100%, that methane has been converted to 39% to carbon disulphide ($CS_2$), and that $CS_2$ and hydrogen ($H_2$) have been produced with a molar $H_2/CS_2$ ratio of 3.07.

In the same way as in example 1, the exiting gases, after cooling to a regulated temperature of 250° C., are introduced into the second reactor, which contains 50 mL of NiMo/alumina catalyst (HR448 from Axens) doped with 11.6% of $K_2O$. The pressure is 3 bar absolute.

Gas-chromatographic analysis of the exiting gases indicates that $CS_2$ has been converted to 100% with a 100% selectivity for methyl mercaptan (or 175 mmol·h$^{-1}$). Moreover, the amount of $H_2S$ recovered at the end of this second step corresponds, within the margins of measurement error, to the amount required for the first step (or approximately 450 mmol·h$^{-1}$). The process according to the invention is an autonomous system which advantageously allows the recycling of the residual compounds to step 1), for example $H_2S$. $CS_2$ and hydrogen were unquantifiable.

This example shows that it is entirely possible to envisage a process for synthesis of methyl mercaptan in which the entirety of the $H_2S$ produced could be recycled, and there would be no need for it to be synthesized for the purposes of said process for synthesis of methyl mercaptan.

The examples below further illustrate the process of the present invention as indicated in example 1 above, but with the first step reproduced with different catalysts.

Example 3

The catalyst of the first step from example 1 was replaced by 30 mL of a catalyst containing 2% by weight of palladium on alumina (Engelhard). The reaction was subsequently carried out at 700° C., 800° C. and 900° C. The results are collated in Table 1.

Example 4

The catalyst from the first step in example 1 was replaced by 60 cm of platinum wire with a diameter of 0.4 mm. The reaction was subsequently carried out at 900° C. The results are collated in Table 1.

Example 5

The catalyst from the first step in example 1 was replaced by 20 superposed sheets (thickness of one sheet=0.152 mm, volume of 20 sheets=0.611 mL) made of platinum and rhodium (Umicore). The reaction was subsequently carried out at 900° C., 1000° C. and 1100° C. The results are collated in Table 1.

Example 6

The catalyst in the first step in example 1 is replaced by 30 mL of catalyst containing 19% by weight of chromium oxide ($Cr_2O_3$) on alumina (T2777, sold by Süd-Chemie). The catalyst underwent a prior sulphurizing treatment with a stream of $H_2S$ (20 $NL·h^{-1}$) for four hours at 900° C., so as to convert the $Cr_2O_3$ into $Cr_2S_3$ and to prevent the formation of oxygenous products during the main reaction of the methane with the $H_2S$. These oxygenous products might interfere in the steps of subsequent recovery of the methyl mercaptan. The reaction was subsequently carried out at 900° C. The results are collated in Table 1 below:

TABLE 1

| Example No | Temperature (° C.) | $CH_4$ conversion % | $CS_2$ selectivity % |
|---|---|---|---|
| 3 | 700 | 9 | 100 |
| 3 | 800 | 12 | 100 |
| 3 | 900 | 18 | 100 |
| 4 | 900 | 11 | 100 |
| 5 | 900 | 30 | 100 |
| 5 | 1000 | 57 | 100 |
| 5 | 1100 | 85 | 100 |
| 6 | 900 | 28 | 100 |

Example 7

The reaction mixture containing methyl mercaptan (MeSH) obtained in example 2 is introduced into a reactor containing dry Amberlyst A21 resin, for producing DMDS in the presence of sulphur, as described in EP976726. Liquid sulphur is introduced into this reactor. The operating pressure is kept at 5.5 bar (0.55 MPa) relative and the temperature at 40° C. The reaction mixture exiting the reactor has the following weight composition apart from excess MeSH and apart from $H_2S$: DMDS 85%, polydimethyl sulphides (PDMS) 15%.

This reaction mixture is then passed into a devolatilizer for treatment. After treatment, the mixture from which the $H_2S$ has been removed is passed into a finishing reactor which contains a charge of dry Amberlyst A21 resin. The pressure and the temperature in the finishing reactor are identical to those of the main reactor.

At the exit of the finishing reactor, the mixture has the following weight composition except for H2S and except for excess MeSH: DMDS 98.5%, PDMS 1.5%. The mixture is then introduced into a devolatilizer for removal of $H_2S$ formed in the reactor during the retrogradation of the polymethyl disulphides by the MeSH to give DMDS.

After the above devolatilization, the mixture is introduced into a distillation column, in which the volatile impurities such as methyl mercaptan (MeSH) and dimethyl sulphide (DMS) are removed at the top of the column. The DMDS collected at the bottom of the column has the following composition by weight:

DMDS: 99.7%
PDMS: 3000 ppm
MeSH: <100 ppm
DMS: <50 ppm

The invention claimed is:

1. A process for preparing dimethyl disulphide, batchwise or continuously, said process comprising at least the following steps:
   a) reacting at least one hydrocarbon charge in the presence of hydrogen sulphide ($H_2S$) and optionally of sulphur (S) to form carbon disulphide ($CS_2$) and hydrogen ($H_2$),
   b) carrying out a hydrogenation reaction of said carbon disulphide ($CS_2$) in the presence of said hydrogen ($H_2$), both obtained in step a), to form methyl mercaptan ($CH_3SH$), hydrogen sulphide ($H_2S$) and optionally hydrogen ($H_2$),
   c) optionally, recycling said hydrogen sulphide ($H_2S$) formed in step b) to step a),
   d) reacting the methyl mercaptan formed in step b) with sulphur to form dimethyl disulphide and hydrogen sulphide,
   e) optionally recycling into step a) the hydrogen sulphide formed in step d), and
   f) recovering the dimethyl disulphide.

2. The process according to claim 1, wherein the hydrocarbon charge is a hydrocarbon charge in gaseous, liquid or solid form and comprises at least one hydrocarbon having a hydrocarbon chain in saturated or unsaturated linear, branched or cyclic form.

3. The process according to claim 1, wherein the hydrocarbon charge comprises at least one alkane.

4. The process according to claim 1, wherein the hydrocarbon charge is methane.

5. The process according to claim 1, wherein the hydrogen sulphide formed in step b) is recycled into step a).

6. The process according to claim 1, wherein hydrogen is formed in step b) and is reacted with sulphur to form hydrogen sulphide.

7. The process according to claim 1, wherein the hydrogen sulphide formed in step d) is recycled into step a).

8. The process according to claim 1, wherein the molar $H_2S$/hydrocarbon charge ratio is between 0.5 and 10, endpoints included.

9. The process according to claim 1, wherein step a) is carried out at a reaction temperature between 500° C. and 1300° C.

10. The process according to claim 1, wherein step b) is carried out at a reaction temperature between 100° C. and 400° C.

11. The process according to claim 1, wherein the co-produced hydrogen is wholly or partly converted to thermal energy.

12. The process according to claim 1, wherein said hydrogen sulphide ($H_2S$) formed in step b) is recycled to step a).

13. The process according to claim 1, wherein the hydrocarbon charge comprises at least one alkane selected from the group consisting of methane ($CH_4$), ethane, propane and butane.

14. The process according to claim 1, wherein the hydrocarbon charge is a hydrocarbon charge in gaseous form.

15. The process according to claim 1, wherein the molar $H_2S$/hydrocarbon charge ratio is between 1 and 3, endpoints included.

16. The process according to claim 1, wherein step a) is carried out at a reaction temperature between 700° C. and 1100° C.

17. The process according to claim 1, wherein step a) is carried out at a reaction temperature between 800° C. and 1000° C.

18. The process according to claim 1, wherein step b) is carried out at a reaction temperature between 200° C. and 300° C.

19. The process according to claim 1, wherein the co-produced hydrogen is wholly or partly converted to thermal energy, the thermal energy being used for the heating of the reaction or reactions of step a), of step b) and/or of step d).

20. The process according to claim 1, wherein all of the hydrogen sulphide consumed in said process is produced in said process.

* * * * *